US009784653B2

(12) United States Patent
Xia et al.

(10) Patent No.: US 9,784,653 B2
(45) Date of Patent: Oct. 10, 2017

(54) APPARATUS AND METHOD FOR PROCESSING A SAMPLE

(71) Applicant: 3M INNOVATIVE PROPERTIES COMPANY, St. Paul, MN (US)

(72) Inventors: Wensheng Xia, Woodbury, MN (US); Jon A. Kirschhoffer, Stillwater, MN (US); Andrew W. Rabins, St. Paul, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/018,436

(22) Filed: Feb. 8, 2016

(65) Prior Publication Data
US 2016/0153874 A1 Jun. 2, 2016

Related U.S. Application Data

(62) Division of application No. 14/001,895, filed as application No. PCT/US2012/027699 on Mar. 5, 2012, now Pat. No. 9,255,864.
(Continued)

(51) Int. Cl.
*G01N 1/30* (2006.01)
*B01L 3/00* (2006.01)
(Continued)

(52) U.S. Cl.
CPC .............. *G01N 1/30* (2013.01); *B01L 3/502* (2013.01); *B01L 3/5023* (2013.01);
(Continued)

(58) Field of Classification Search
CPC ......... B01L 2200/026; B01L 2200/028; B01L 2200/10; B01L 2300/0681;
(Continued)

(56) References Cited

U.S. PATENT DOCUMENTS 5,733,449 A * 3/1998 Bowers ................ B01D 61/18
210/321.6
2002/0125197 A1 9/2002 Hager et al.
(Continued)

FOREIGN PATENT DOCUMENTS

EP     1 588 764      10/2005
EP     1 953 552      8/2008
(Continued)

OTHER PUBLICATIONS

Berry, E.D. et al.; "Hydroxyapatite Adherence as a Means to Concentrate Bacteria"; Applied and Environmental Microbiology; vol. 63, No. 10; 1997; pp. 4069-4074.
(Continued)

*Primary Examiner* — Nathan Bowers
*Assistant Examiner* — Lydia Edwards
(74) *Attorney, Agent, or Firm* — 3M Innovative Properties Company; Eric E. Silverman

(57) ABSTRACT

A first apparatus for processing a liquid sample is disclosed. The apparatus includes a sample-receiving, a filtrate-receiving component, and an analyte-capture element. The apparatus forms a liquid flow path through which the sample passes, thereby causing the analyte-capture element to capture an analyte, if present. A method is disclosed whereby a liquid sample is passed through the first apparatus and the analyte-capture element is easily separated from the apparatus for further processing and detection of the analyte. A structurally-related second apparatus for processing a plurality of liquid samples, and a corresponding method of use, also is disclosed.

14 Claims, 9 Drawing Sheets

Related U.S. Application Data

(60) Provisional application No. 61/451,096, filed on Mar. 9, 2011.

(51) Int. Cl.
*C12N 15/10* (2006.01)
*G01N 1/34* (2006.01)

(52) U.S. Cl.
CPC ...... *B01L 3/50255* (2013.01); *C12N 15/1017* (2013.01); *G01N 1/34* (2013.01); *B01L 2200/026* (2013.01); *B01L 2200/028* (2013.01); *B01L 2200/10* (2013.01); *B01L 2300/069* (2013.01); *B01L 2300/0681* (2013.01); *B01L 2300/0832* (2013.01); *B01L 2300/0861* (2013.01); *B01L 2300/0887* (2013.01); *B01L 2400/049* (2013.01)

(58) Field of Classification Search
CPC ....... B01L 2300/069; B01L 2300/0832; B01L 2300/0861; B01L 2300/0887; B01L 2400/049; B01L 3/502; B01L 3/5023; B01L 3/50255; C12N 15/1017
See application file for complete search history.

(56) References Cited

U.S. PATENT DOCUMENTS

| | | |
|---|---|---|
| 2003/0080454 A1 | 5/2003 | Moll et al. |
| 2003/0091989 A1 | 5/2003 | Davis et al. |
| 2004/0158188 A1 | 8/2004 | Kauffmann et al. |
| 2005/0045538 A1 | 3/2005 | Seto et al. |
| 2005/0103703 A1 | 5/2005 | Young et al. |
| 2007/0298451 A1 | 12/2007 | Ribault et al. |
| 2008/0299621 A1* | 12/2008 | Tatnell ............... C12N 15/1017 435/91.1 |
| 2010/0209961 A1 | 8/2010 | Kshirsagar et al. |

FOREIGN PATENT DOCUMENTS

| | | |
|---|---|---|
| JP | 2005-17281 | 1/2005 |
| JP | 2005-95157 | 4/2005 |
| WO | WO 93/11221 | 6/1993 |
| WO | WO 96/41810 | 12/1996 |
| WO | WO 97/08306 | 3/1997 |
| WO | WO 2008/134472 | 11/2008 |
| WO | WO 2009/046191 | 4/2009 |
| WO | WO 2010/075116 | 7/2010 |
| WO | WO 2010/078234 | 7/2010 |
| WO | WO 2012/092123 | 7/2012 |

OTHER PUBLICATIONS

Oster, J. et al.; "Polyvinyl-alcohol-based magnetic beads for rapid and efficient separation of specific or unspecific nucleic acid sequences"; Journal of Magnetism and Magnetic Materials; vol. 225; 2001; pp. 145-150.

* cited by examiner

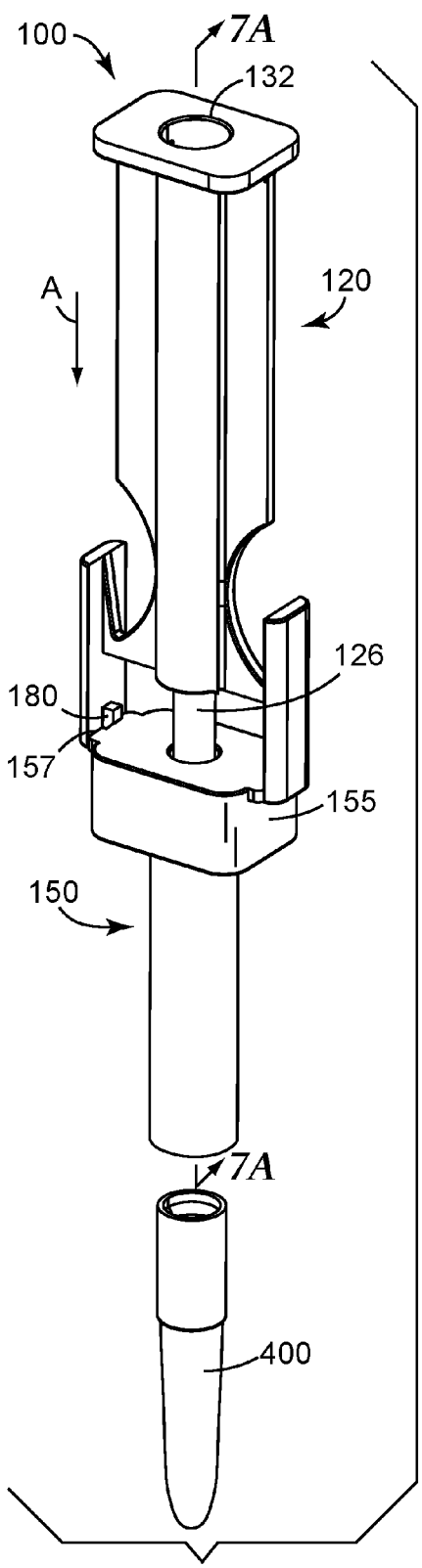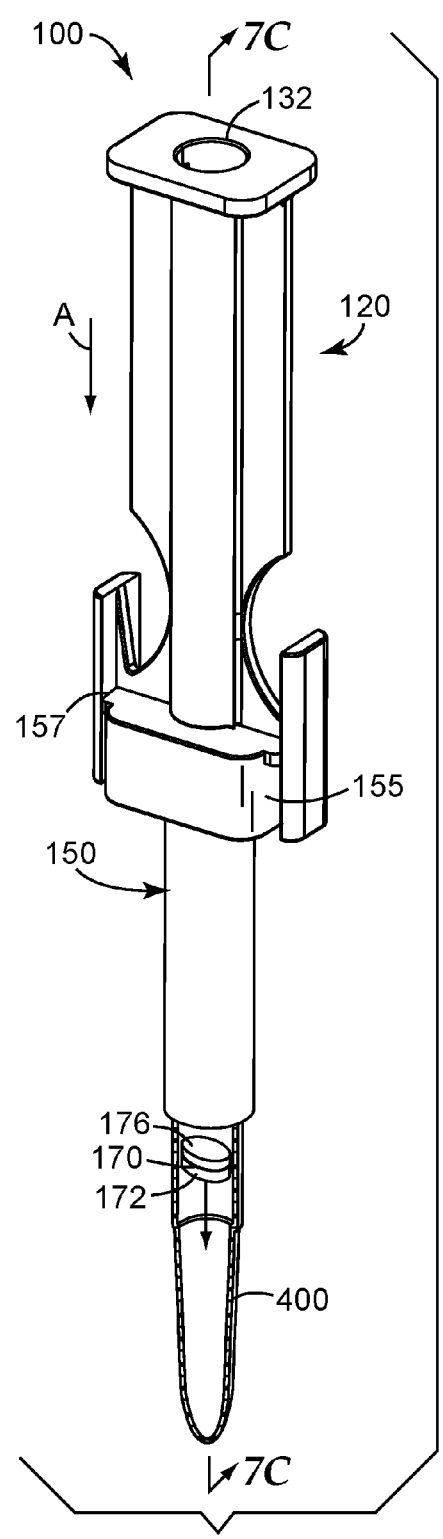
FIG. 2B
FIG. 2C

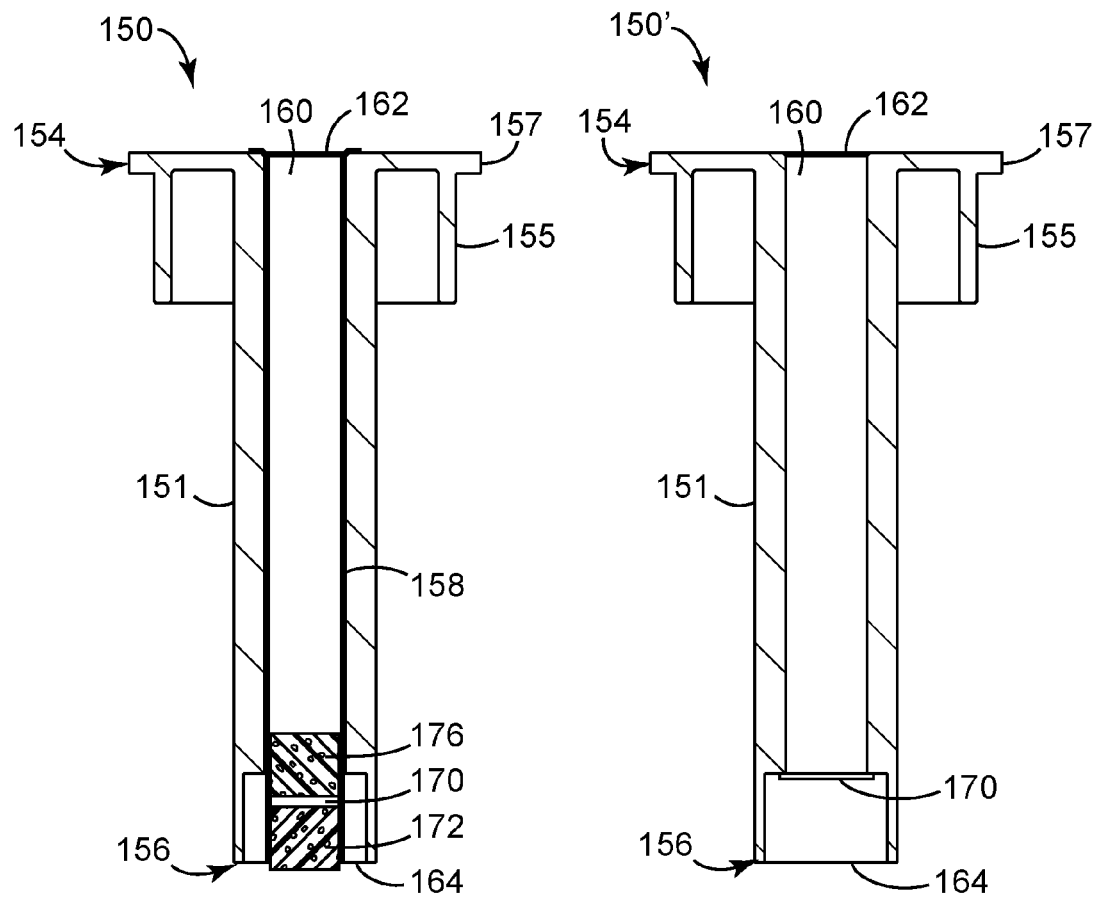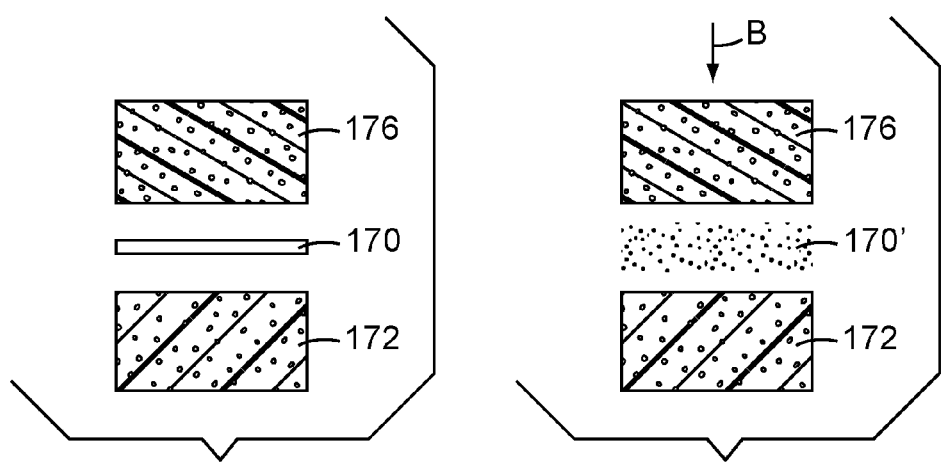

APPARATUS AND METHOD FOR PROCESSING A SAMPLE

CROSS REFERENCE TO RELATED APPLICATION

This application is a divisional of U.S. patent application Ser. No. 14/001,895, filed Aug. 28, 2013, now U.S. Pat. No. 9,255,864, which is a national stage filing under 35 U.S.C. 371 of PCT/2012/027699, filed Mar. 5, 2012, which claims priority to U.S. Provisional Patent Application No. 61/451,096, filed Mar. 9, 2011, which are incorporated herein by reference in their entirety.

BACKGROUND

Many types of samples (e.g., clinical, environmental, food, and beverage samples) are routinely tested for the presence or absence of microorganisms. In particular many samples are tested for the presence of pathogenic microorganisms. Often, the samples require various types of pretreatment (i.e., processing prior to a detection step) in order to increase the number of target microorganisms, decrease, the number of non-target microorganisms, concentrate the microorganisms, and/or reduce the quantity of potentially-interfering material in the sample. The pre-treatment steps may be laborious and can take several hours to several days to complete. A variety of materials and devices have been developed to reduce the number of steps and the time that it takes to complete the pre-treatment of samples.

Processing a plurality of samples simultaneously can be difficult because of the lack of simple, efficient devices for the procedure. There remains a need for simple, methods to prepare one or more samples for the detection of microorganisms.

SUMMARY

In general, the invention is directed to the detection of a microorganism in a sample. In particular, the present disclosure provides a first apparatus and a corresponding method of use for processing a sample to detect the presence or absence of an analyte associated with a microorganism. Advantageously, the first apparatus is configured such that it can reduce the amount of interfering material in the sample and concentrate the analyte in one simple step. The concentrated analyte can then be transferred to a container for subsequent processing in another simple step. The present disclosure provides a second apparatus and a corresponding method of use for processing a plurality of samples to detect the presence or absence of an analyte associated with a microorganism in two or more samples. In addition to the advantages provided by the first apparatus, the second apparatus permits the simultaneous transfer of a plurality of concentrated analytes to containers for subsequent processing.

In one aspect, the present disclosure provides an apparatus for processing a sample. The apparatus can comprise a sample-receiving component, a filtrate-receiving component, and an analyte-capture element. The sample-receiving component can comprise a first hollow body with first end, a second end, and a first chamber extending from the first end to the second end; and a filter element disposed in the first chamber between the first and second ends. The first end can include a first opening configured to receive a sample and the second end can include a second opening The filtrate-receiving component can comprise a second hollow body with a third end, a fourth end, and a second chamber extending from the third end to the fourth end. The third end can include a third opening configured to receive the second end of the sample-receiving member and the fourth end can include a fourth opening. The analyte-capture element can be removably coupled to the filtrate-receiving component. When the sample-receiving component is coupled to the filtrate-receiving component, the apparatus can form a flow path that facilitates fluid passage through the first chamber, the filter element, and the second chamber, the flow path facilitating contact between a fluid sample and the analyte-capture element. The second end can be shaped and proportioned to fit within and move longitudinally through at least a portion of the second chamber.

In any of the above embodiments the analyte-capture element further can be disposed in the second chamber.

In any of the above embodiments, the apparatus further can comprise a removable inner sleeve with a fifth end having a fifth opening and a sixth end having a sixth opening, wherein the sleeve is disposed in the second chamber. In any of the above embodiments, the apparatus further can comprise a porous support or a porous shield. In any of the above embodiments, at least a portion of the porous support or porous shield can be disposed in the second hollow body between the analyte-capture element and the fourth opening.

In any of the above embodiments, the filter element further can comprise a plurality of layers In any of the above embodiments, the second end can be adapted to be inserted into the second chamber and moved through the second chamber to a point at which it contacts the analyte-capture element, porous support, or porous shield.

In another aspect, the present disclosure provides an apparatus for processing a plurality of samples. The apparatus can comprise a sample-receiving component, a filtrate-receiving component, and a plurality of analyte-capture elements. The sample-receiving component can comprise a first body with first end, a second end, and a plurality of spaced-apart first chambers, each first chamber extending from the first end to the second end; and a plurality of filter elements, each filter element disposed between the first and second openings in one of the plurality of first chambers. The first end can comprise a plurality of first openings, at least one first opening configured to receive a sample. The second end can comprise a plurality of outlets, each outlet having a second opening. The first body can form a plurality of fluid pathways, each pathway extending from a first opening to a second opening and through a first chamber there between. The filtrate-receiving component can comprise a second body with a third end, a fourth end, and a plurality of spaced-apart second chambers, each second chamber extending from the third end to the fourth end. Each second chamber can comprise a third opening at the third end, the third opening configured to receive one of the plurality of outlets; and a fourth opening at the fourth end. Each of the plurality of analyte capture elements can be coupled to the filtrate-receiving component. When the sample-receiving component is coupled to the filtrate-receiving component, the apparatus can form a plurality of flow paths; each flow path facilitating fluid passage through one of the plurality of first chambers, one of the plurality of filter elements, and one of the plurality of second chambers, and facilitating fluid contact with at least one of the plurality of analyte-capture elements. Each of the plurality of outlets can be shaped and proportioned to fit within and move longitudinally through at least a portion of the second chamber. In any embodiment, at least one of the plurality of analyte-capture elements further can be disposed in at least one of the plurality of second chambers. In any embodiment, the apparatus further can comprise at least one removable inner sleeve with a fifth end having a fifth opening and a sixth end having a sixth opening, wherein the sleeve is disposed in at least one of the plurality of second chambers. In any embodiment, the apparatus further can comprise a porous support or a porous shield. In any embodiment, at least a portion of the at least one porous support can be disposed in at least one second chamber between the analyte-capture element and the fourth end. In any embodiment, the analyte-capture element can be coupled to the porous support. In any embodiment, at least one filter element further can comprise a plurality of layers. In any embodiment, each of the plurality of outlets can be adapted to be inserted into one of the plurality of second chambers and moved through the second chamber to a point at which it contacts the analyte-capture element, porous support, or porous shield.

In any of the above embodiments, the fourth end can be configured to couple to a source of negative pressure. In any of the above embodiments, the sample receiving component or the filtrate-receiving component further can comprise a positioning element that, when the sample-receiving component is coupled to the filtrate-receiving component, controllably retains a position of the sample-receiving component relative to the filtrate-receiving component.

In yet another aspect, the present disclosure provides a method of detecting the presence or absence of an analyte in a sample. The method can comprise providing a liquid sample and an apparatus for processing a sample. The apparatus can comprise a sample-receiving component, a filtrate-receiving component, and an analyte-capture element. The sample-receiving component can comprise a first hollow body with first end, a second end, and a first chamber extending from the first end to the second end; and a filter element disposed in the first chamber between the first and second ends. The first end can include a first opening configured to receive a sample and the second end can include a second opening. The filtrate-receiving component can comprise a second hollow body with a third end, a fourth end, and a second chamber extending from the third end to the fourth end. The third end can include a third opening configured to receive the second end of the sample-receiving member and the fourth end can include a fourth opening. The analyte-capture element can be removably coupled to the filtrate-receiving component. When the sample-receiving component is coupled to the filtrate-receiving component, the apparatus can form a flow path that facilitates fluid passage through the first chamber, the filter element, and the second chamber, the flow path facilitating contact between a fluid sample and the analyte-capture element. The second end can be adapted to be inserted into the second chamber and moved through a portion of the second hollow body. The method further can comprise passing the liquid sample through the filter element, contacting the filtered liquid with the analyte-capture element, separating the analyte-capture element from the apparatus, and detecting the presence or absence of the analyte.

In any of the above embodiments, the method further can comprise attaching the apparatus to a source of negative pressure, wherein passing the liquid sample through the filter element further comprises using a negative pressure to draw the sample through the filter element to produce a filtered sample. In any of the above embodiments of the method, using negative pressure to draw the sample through the filter element further can comprise using the negative pressure to contact the filtered sample with the analyte-capture element. In any of the above embodiments of the method, separating the analyte-capture element from the apparatus further can comprise using the second end to separate the analyte-capture element from the apparatus. In any of the above embodiments of the method, using the second end further can comprise urging the second end through the second chamber to separate the analyte-capture element. In any of the above embodiments, the method further can comprise, after separating the analyte-capture element, treating the analyte capture element with a cell lysis agent.

In yet another aspect, the present disclosure provides a method of detecting the presence or absence of an analyte in a plurality of samples. The method can comprise providing a plurality of liquid samples and an apparatus. The apparatus can comprise a sample-receiving component, a filtrate-receiving component, and a plurality of analyte-capture elements. The sample-receiving component can comprise a first body with first end, a second end, and a plurality of spaced-apart first chambers, each first chamber extending from the first end to the second end; and a plurality of filter elements, each filter element disposed between the first and second openings in one of the plurality of first chambers. The first end can comprise a plurality of first openings, at least one first opening configured to receive a sample. The second end can comprise a plurality of outlets, each outlet having a second opening. Each of the plurality of first chambers can form a fluid pathway from one of the plurality of first openings to one of the plurality of second openings The filtrate-receiving component can comprise a second body with a third end, a fourth end, and a plurality of spaced-apart second chambers, each second chamber extending from the third end to the fourth end. Each second chamber can comprise a third opening at the third end, the third opening configured to receive one of the plurality of outlets; and a fourth opening at the fourth end. Each of the plurality of analyte capture elements can be coupled to the filtrate-receiving component. When the sample-receiving component is coupled to the filtrate-receiving component, the apparatus can form a plurality of flow paths; each flow path facilitating fluid passage through one of the plurality of first chambers, one of the plurality of filter elements, and one of the plurality of second chambers, and facilitating fluid contact with at least one of the plurality of analyte-capture elements. Each of the plurality of outlets can be adapted to be inserted into one of the plurality of second chambers and moved through a portion of the second chamber. The method further can comprise passing at least two liquid sample through at least two of the plurality of filter elements to generate at least two filtered liquids, contacting the at least two filtered liquids with at least two analyte-capture elements, separating the at least two analyte-capture elements from the apparatus, and detecting the presence or absence of the analyte. In any of the embodiments, the method further can comprise attaching the apparatus to a source of negative pressure, wherein passing the plurality liquid samples through the at least two filter elements further comprises using a negative pressure to draw the liquid samples through the at least two filter elements to produce at least two filtered samples. In any of the embodiments of the method, using negative pressure to draw the plurality of samples through the at least two filter elements further can comprise using the negative pressure to contact the filtered samples with the at least two analyte-capture elements. In any of the embodiments, separating the at least two analyte-capture elements from the apparatus further can comprise using at least two outlets to separate the at least two analyte-capture element from the apparatus. In any of the embodiments, using the at least two outlets further can comprise urging the at least two outlets through the at least two second chambers to separate the at least two analyte-capture elements from the apparatus. In any of the above embodiments, the method further can comprise, after separating the at least two analyte-capture elements, treating the at least two analyte capture element with a cell lysis agent.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

FIG. 2B is a partially-exploded perspective view of the apparatus of FIG. 2A in a first operational configuration and a container used therewith.

FIG. 2C is a perspective view, partially in section, of the assembled apparatus and container of FIG. 2B in a second operational configuration.

FIG. 5A is a cross-sectional side view of the filtrate-receiving component of the apparatus of FIG. 1.

FIG. 5B is a partial side view of one embodiment of a filtrate-receiving component with an analyte-capture element coupled thereto.

FIG. 6A is an exploded side view of one embodiment of an analyte-capture element disposed between a porous support and a porous shield.

FIG. 6B is an exploded side view of another embodiment of an analyte-capture element disposed between a porous support and a porous shield.

DETAILED DESCRIPTION

Figure 1:
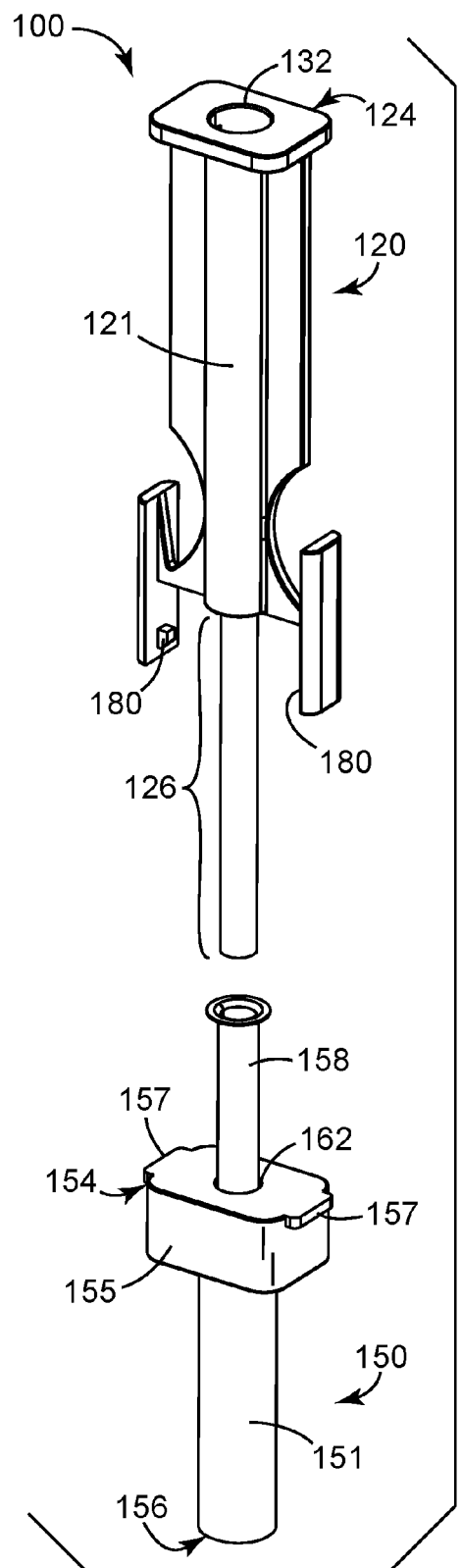
FIG. 1 is a partially-exploded perspective view of one embodiment of an apparatus for processing a sample, according to the present disclosure.

The present disclosure generally relates to preparing a sample to detect the presence or absence of an analyte. In particular, the present disclosure provides an apparatus and a method to facilitate the removal of relatively large, particulate material from a liquid sample and to capture the analyte for subsequent analysis. Advantageously, the analyte capture may be accomplished with the apparatus using just one or two steps. The resulting captured analyte is relatively concentrated, relatively free of impurities, and is suitable for use in a variety of detection methods (e.g., immunodetection methods and nucleic acid detection methods).

The present disclosure includes methods and an apparatus for processing a single sample. The present disclosure further includes a method and an apparatus for processing simultaneously a plurality of samples. The inventive methods relate to the detection of an analyte in a sample. In any embodiment, the analyte can be a biological analyte such as, for example, a biological analyte that indicates the presence of a microorganism in the sample.

The sample can be any sample that may comprise a biological analyte. Nonlimiting examples of suitable samples include suspensions or cultures of cells (e.g., mammalian cells, insect cells, yeast cells, filamentous fungi, bacterial cells), environmental samples (e.g., surface swabs), food (e.g., raw materials, in-process samples, and finished-product samples), beverages, clinical samples (e.g., blood, urine, sputum, tissue, mucous, feces, wound exudate, pus), and water (e.g., surface water, potable water, process water).

Non-limiting examples of suitable biological analytes include nucleic acids (e.g., a polynucleotide associated with a particular type of cell or microorganism) or detectable antigens (e.g., proteins, oligopeptides, enzymes, endotoxin, cell membrane components, and cell wall components). Analytical procedures to detect the biological analytes are known in the art. Preferred biological analytes to be detected include nucleic acids that are capable of being amplified in a reaction (e.g., PCR), for example.

Besides fluid samples, other test samples may include liquids as well as solid(s) dissolved or suspended in a liquid medium. Samples of interest may include process streams, water, soil, plants or other vegetation, air, surfaces (e.g., contaminated surfaces), and the like. Samples can also include cultured cells. Samples can also include samples on or in a device comprising cells, spores, or enzymes (e.g., a biological indicator device).

Solid samples may be disintegrated (e.g., by blending, sonication, homogenization) and may be suspended in a liquid (e.g., water, buffer, broth). In some embodiments, a sample-collection device (e.g., a swab, a sponge) containing sample material may be used in the method. Alternatively, the sample material may be eluted (e.g., rinsed, scraped, expressed) from the sample-collection device before using the sample material in the method. In some embodiments, liquid or solid samples may be diluted in a liquid (e.g., water, buffer, broth).

Suitable samples also include cell-suspension media (e.g., culture broth, semi-solid cell culture media, and tissue culture media, filtrate) that contain cells or previously contained cells. Suitable samples also include cell lysates. Cell lysates may be produced by chemical means (e.g., detergents, enzymes), mechanical means (sonic vibration, homogenization, French Press), or by other cell lytic means known in the art.

Microorganisms (e.g., bacteria, fungi, viruses) are a source of detectable analytes. Microorganisms can be analyzed in a test sample that may be derived from a variety of sources, as described herein. Microorganisms of particular interest include prokaryotic and eukaryotic organisms, particularly Gram positive bacteria, Gram negative bacteria, fungi, protozoa, mycoplasma, yeast, viruses, and even lipid-enveloped viruses. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis, Streptococcus pneumoniae, S. agalactiae, S. pyogenes, Enterococcus faecalis,* Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis, Pseudomonas aeruginosa, Escherichia coli, Aspergillus niger, A. fumigatus, A. clavatus, Fusarium solani, F. oxysporum, F. chlamydosporum, Listeria monocytogenes, Listeria ivanovii, Vibrio cholera, V. parahemolyticus, Salmonella cholerasuis, S. typhi, S. typhimurium, Candida albicans, C. glabrata, C. krusei, Enterobacter sakazakii, E. coli* O157 and multiple drug resistant Gram negative rods (MDR).

Gram positive and Gram negative bacteria are of particular interest. Of even more interest are Gram positive bacteria, such as *Staphylococcus aureus*. Also, of particular interest are antibiotic resistant microbes including MRSA, VRSA, VISA, VRE, and MDR.

FIG. 1 shows an exploded upper perspective view of one embodiment of an first apparatus 100 according to the present disclosure. The first apparatus 100 comprises a sample-receiving component 120 and a filtrate-receiving component 150. The sample-receiving component 120 comprises a first hollow body 121 with a first end 124 and a second end 126 opposite the first end 124. The first end includes a first opening 132. The first opening is configured to receive a sample. For example, the first opening 132 can be dimensioned to receive a pipette tip, through which a liquid sample can be transferred into the first hollow body 121.

Figure 2A:
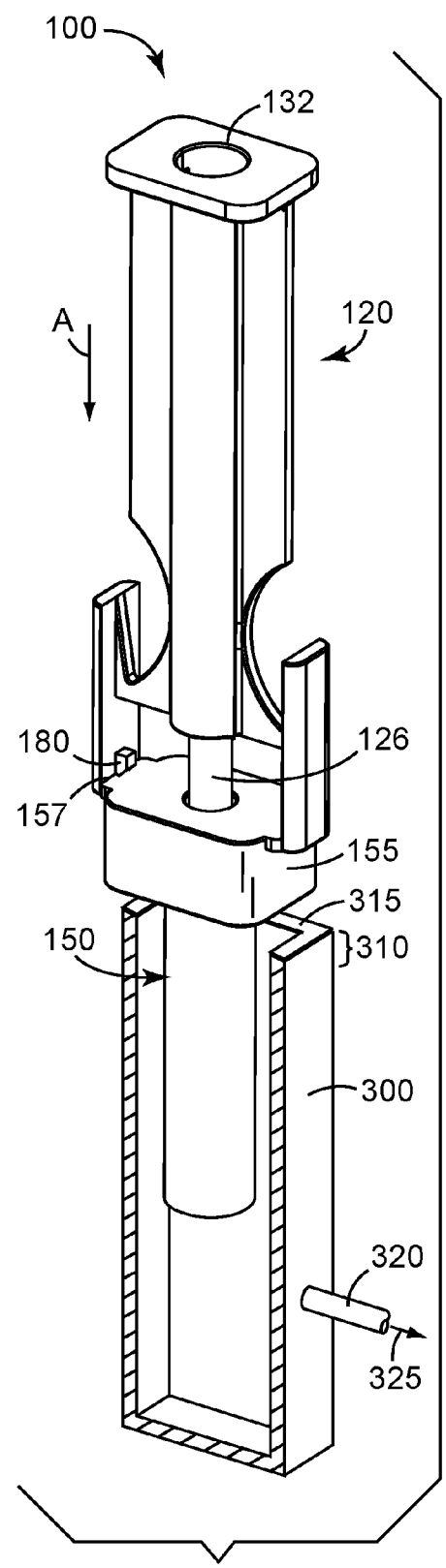
FIG. 2A is a perspective view, partially in section, of the assembled apparatus of FIG. 1 operationally coupled to a receptacle that is connected to a source of negative pressure.

The sample-receiving component 120 further comprises optional positioning elements 180. The positioning element 180 can function temporarily (e.g., while a sample is being loaded and/or processed) to maintain the sample-receiving component 120 in a substantially fixed position relative to the filtrate receiving component 150. The positioning element 180 may function cooperatively with a structure found on the filtrate-receiving component 150, as shown in FIG. 2. In some embodiments, the second end 126 first hollow body 121 can be inserted into the third opening 162 and moved into the second hollow body 151 until the positioning element 180 reaches a first position (e.g., positioning element 180 contacts the collar 155) relative to the filtrate-receiving component 150, as shown in FIG. 2A. It will be appreciated that other structures and/or configurations of positioning elements can be used to accomplish the same function (i.e., temporarily holding the sample-receiving component 120 in a fixed location relative to the filtrate-receiving component 150).

Also shown in FIG. 1 is an optional liner 158. If present, the liner 158 is dimensioned to be inserted into the third opening 162 and moved into the second hollow body 151. The liner 158 can be fabricated using polymeric materials (e.g., polyethylene, polypropylene) using molding or extrusion processes known in the art. The liner 158 is tubular (i.e., having openings at each end of its longitudinal axis) and, preferably, has an outer diameter that is slightly smaller than the inner diameter of the second hollow body 151. The liner 158 can be slideably inserted into the second hollow body 151 for use. Optionally, the opening at one end of the liner 158 can include a flange to prevent further movement of the liner 158 into the second hollow body 151 and for convenient handling of the liner 158 during insertion or removal of the liner from the second hollow body 151.

The filtrate-receiving component 150 comprises a second hollow body 151 with a third end 154 and a fourth end 156 opposite the third end 154. The third end 154 includes a third opening 162. The third opening 162 is dimensioned to receive the second end 126 of the sample-receiving component 120. When the first apparatus 100 includes the optional liner, the second end 126 of the sample-receiving component is dimensioned to be inserted into the liner 158. The filtrate-receiving component 150 further comprises an optional collar 155, which can facilitate coupling the first apparatus 100 to a source of negative pressure, as shown and described herein. Optionally, the collar 155 can further comprise tabs 157 to act in concert with the positioning element 180 to maintain the position of the sample-receiving component 120 relative to the filtrate-receiving component 150, as shown in FIG. 2A.

FIG. 2A shows a side view, partially in section of the assembled first apparatus 100 of FIG. 1 operationally coupled to a waste receptacle 300. The first apparatus 100 is shown in a first operational configuration, as shown and described in more detail below. In this configuration, the second end (not shown) of the sample-receiving component 120 is inserted into the filtrate-receiving component 150 and the first apparatus 100 is ready to receive a sample into the first opening 132. It can be seen that, in this configuration, the positioning element 180 contacts the tab 157, thereby providing moderate resistance (e.g., resistance that can be overcome by moderate manual force) to the movement of the sample-receiving component 120 toward the filtrate-receiving component 150 in the direction indicated by arrow "A". The positioning element 180 prevents further movement of the first hollow body 121 into the second hollow body 151 until the sample-receiving component 120 and filtrate-receiving component 150 are urged together with enough force to deflect the positioning element 180 outward from the collar 155 (i.e., approximately perpendicular to arrow "A"), thereby allowing the second end 126 of the first hollow body 121 to move further into the filtrate-receiving component 150.

The waste receptacle 300 includes a docking portion 310 with an opening configured to receive the filtrate-receiving component 150 of the first apparatus 100. The docking portion 310 includes an optional gasket 315. The waste receptacle 300 is operationally connected to a conduit 320 (e.g., a pipe or hose) that is coupled to a source of negative pressure 325. The waste receptacle 300 can be fabricated from plastic, metal, or glass, for example, and is sufficiently sturdy to maintain its integrity when the interior of the receptacle 300 is subjected to negative pressure (e.g., up to about 520 torr). In use, the collar 155 of the first apparatus 100 is slideably moved onto the docking portion 310 to create a substantially air-tight seal and the source of negative pressure 325 is actuated to draw a liquid sample through the first apparatus 100 as shown and described herein.

FIG. 2B shows a partially-exploded perspective view of the assembled first apparatus 100 of FIG. 2A with a container 400 (e.g., a test tube, a micro test tube, or the like) attached to the fourth end 156 of the filtrate-receiving component 150. When fully assembled, the container 400 is detachably attached (e.g., by friction fit) to a fourth opening (not shown, see FIG. 10) of the filtrate-receiving component 150 and is positioned with the container opening facing the fourth opening of the filtrate-receiving component 150.

FIG. 2C shows a perspective view of the assembled first apparatus 100 of FIG. 2B in a second operational configuration. The container 400 is inserted into the fourth opening 164 of the filtrate-receiving component 150. It can be seen that, in this operational configuration, the second end 126 of the sample-receiving component 120 is fully-inserted into the filtrate-receiving component.

Figure 3:
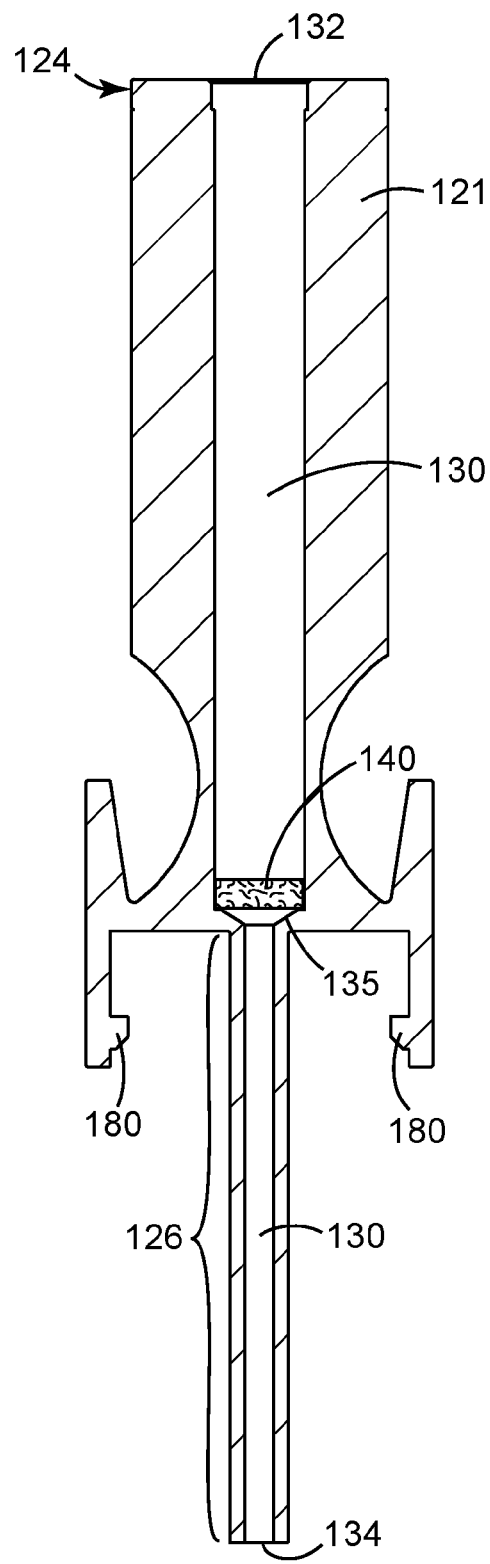
FIG. 3 is a cross-sectional side view of the sample-receiving component of the apparatus of FIG. 1.

FIG. 3 shows a cross-sectional side view of the sample-receiving component 120 of FIG. 1. The sample-receiving component 120 comprises a first hollow body 121 with a first chamber 130 extending from the first end 124 to the second end 126. The first end 124 includes the first opening 132. The second end 126 includes a second opening 134. The first chamber 130 is cylindrical in the illustrated embodiment, although other shapes may be suitable. It can be seen that the portion of the first chamber 130 proximate the first end 124 has a larger diameter than the portion of the first chamber proximate the second end 126. This feature is not required, although it may be desirable in some embodiments. The first chamber 130 forms a liquid flow path from the first opening 132 to the second opening 134. The second opening 134 is smaller than the first opening 132. Because the second opening 134 is smaller than the inner diameter of the first hollow body 121, a platform 135 is formed at the second end 126 of the first hollow body 121. The platform 135 forms a support for filter element 140. Although the illustrated embodiment shows the platform 135 located proximate the second end 126, it is contemplated that, in some embodiments, the platform 135 may be located at a position that is closer to the first end 124 of the hollow body 121. Also shown in FIG. 3 is positioning element 180 described herein.

The first hollow body 121 can be fabricated by injection molding, for example, from polymeric material (e.g., polyethylene, polypropylene, polystyrene, polycarbonate). Alternatively, the first hollow body 121 can be fabricated using glass or metal.

The filter element 140 serves as a prefilter to trap and retain relatively large (e.g., ≥5 µm diameter) particulate materials from a liquid sample passing there through. The sample-receiving component 120 is configured such that a liquid sample moving through the first chamber 130 from the first opening 132 to the second opening 134 passes through the filter element 140. The filter element 140 is supported by the platform 135 and, optionally, may be coupled (e.g., via an adhesive or other secural means, not shown) to the platform 135.

The filter element 140 can be constructed from a variety of materials known in the art (e.g., nonwoven materials comprising nylon, polypropylene, glass, or cellulose acetate fibers, for example; or perforated films such as polycarbonate films, for example). In any embodiment, the filter element 140 may comprise a single layer of material. In some embodiments, the filter element 140 may comprise a plurality of layers. A layer of a filter element comprising a plurality of layers may comprise a particulate material to facilitate the removal of certain materials from the sample.

Figure 4:
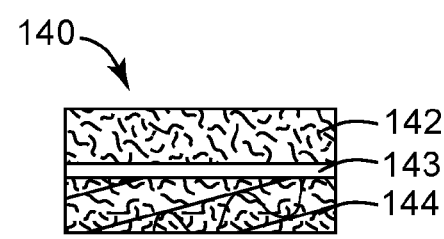
FIG. 4 is a side view of one embodiment of a filter element according to the present disclosure.

FIG. 4 shows one embodiment of a filter element 140 comprising a plurality of layers. Line A shows the direction of fluid flow through the filter element 140. Layer 142 is the first layer of a multi-layer filter element 140 through which a sample passes. Layer 142 may comprise a membrane filter or a relatively coarse nonwoven depth filter (approximately 1 mm thick) made from polyethylene fibers. Layer 142 may have a nominal porosity of approximately 20-50 µm and can function to prevent the passage of large particles into the other layers of filter element 140. Layer 143 may comprise a wet-laid fibrous scaffold (approximately 0.2-1 mm thick), optionally containing particulate material that removes a one or more specific non-analyte materials (e.g., fats, minerals) from the liquid sample. Although layer 143 can have a nominal porosity (e.g., 10-20 µm) that further removes particulate matter from the sample, the fibrous and/or particulate material also may selectively remove fatty components from the liquid sample without substantially removing bacteria from the liquid. Layer 144 comprises a filter material that functions to substantially remove particulate materials that are larger than a bacterium (e.g., ≥5 µm diameter). A non-limiting example of a material that may be used in a filter element 140 individually or in any combination with other materials is a polypropylene felt filter (part number NB005PPS2R, 5 µm nominal porosity, available from CUNO 3M, Meriden, Conn.). Other known layers (not shown) and/or materials may be used in filter element 140, with each layer functioning to reduce the amount of non-analyte material in the liquid sample as it passes through the filter element 140.

FIG. 5A shows a cross-sectional side view of the filtrate-receiving component 150 of FIG. 1. The filtrate-receiving component 150 comprises a second hollow body 151 with liner 158 disposed therein. The second hollow body 151, with the optional liner 158 positioned therein, forms a second chamber 160 extending from the third end 154 to the fourth end 156. The third end includes a third opening 162. The fourth end 156 includes a fourth opening 164. Thus, the second chamber 160 forms a liquid flow path extending from the third opening 162 to the fourth opening 164 of the second hollow body 151. The second hollow body 151 further comprises the collar 155 at the third end 154. During use, the collar 155 can be coupled to a container operationally connected to a source of negative pressure (as shown in FIG. 2) to facilitate the movement of liquid through the first apparatus 100.

The second hollow body 151 can be fabricated by injection molding, for example, from polymeric material (e.g., polyethylene, polypropylene, polystyrene, polycarbonate). Alternatively, the second hollow body 151 can be fabricated using glass or metal.

Detachably coupled to the filtrate-receiving component 150 is an analyte-capture element 170. In the illustrated embodiment of FIG. 5A, the analyte capture element 170 is disposed in the second chamber 160 proximate the fourth end 156. The analyte capture element 170 is disposed between an optional porous support 172, which is proximate the fourth opening 164, and an optional porous shield 176. The porous support 172, when present, functions to provide a structure on which to retain a particulate and/or relatively non-rigid analyte-capture element 170 in position as a liquid sample flows adjacent and/or through the analyte-capture element 170.

Both the porous support 172 and the porous shield 176 can be made from a variety of porous materials such as, for example, cellulosic fibers, synthetic fibers (e.g., polymeric, glass), foams (e.g., open-cell foams such as, for example, polyurethane), and porous frits (e.g., glass, ceramic, polymeric) that permit the passage of liquid (e.g., an aqueous liquid) there through. Preferably, the porous shield 176, when present, comprises material with nominal porosity greater than about 5 µm, preferably greater than about 10 µm, so that microorganisms can pass freely through the material to the analyte-capture element 170. A non-limiting example of a material that may be used in a porous shield 176 is a polypropylene felt filter (part number NB005PPS2R, 5 µm nominal porosity, available from CUNO 3M, Meriden, Conn.).

The porous support 172, analyte-capture element 170, and porous shield 176 are dimensioned such that they can be slideably inserted (e.g., by press-fit) into and releasably retained in the liner 158 or the second hollow body 151. In some embodiments (not shown), the analyte-capture element 170 may be coupled (e.g., adhesively coupled, stitched, heat-bonded) to the porous support 172 and/or the porous shield 176, provided the coupling means does not substantially prevent contact between a liquid sample and the analyte-capture element 170 and/or substantially prevent the flow of a liquid sample through the analyte-capture element 170.

The analyte-capture element 170 comprises material configured to capture and retain a target analyte. In some embodiments, the analyte-capture element 170 comprises a porous filter that allows the passage of liquids but retains particles that are approximately the size of bacteria (about 0.5 to about 5 µm). The analyte-capture element 170 can be one or more of a variety of membrane-type filters (e.g., cellulose acetate filters, nylon filters, nitrocellulose filters, polycarbonate filters, ceramic filters), for example. Non-limiting examples of suitable membrane-type filters are the VERSAPOR 3000TN membrane (3 µm nominal porosity) and the VERSAPOR 800 membrane (0.8 µm nominal porosity), both available from Pall Life Sciences, Port Washington, N.Y.) Optionally, the filter material may comprise a binding partner (e.g., a polyclonal antibody, a monoclonal antibody, a receptor, a lectin) coupled thereto. In some embodiments, the binding partner may provide the specificity for binding a particular target analyte. FIG. 6A shows an exploded view of one configuration of an analyte-capture element 170 comprising a porous filter. The analyte-capture element 170 (e.g., a 0.45 µm membrane filter) is sandwiched between a porous support 172 and a porous shield 176. Both the porous support 172 and the porous shield 176 can be formed, for example, by using a punch die to cut a foam material (e.g., polyurethane foam) to a diameter that will allow it to form a friction fit with the walls of the second chamber 160.

Alternatively, or additionally, the analyte-capture element 170' may comprise a particulate material (e.g., a fiber, a particle, a bead) or a nonporous sheet material (e.g., a polymer film) configured to bind to a target analyte. In some embodiments, the particulate material may be porous. In some embodiments, the particulate material may be nonporous. In some embodiments, the analyte-capture element 170 may comprise a combination of porous and nonporous particulate materials.

In some embodiments, the particulate material may bind the target analyte relatively non-specifically. Certain particulate cell concentration agents are known in the art and are suitable for use in methods of the present disclosure. Nonlimiting examples of suitable cell concentration agents include activated charcoal, hydroxyapatite (Berry et al.; Appl. Environ. Microbiol.; 63:4069-4074; 1997), magnetic beads (Oster et al., J. Magnetism and Magnetic Mat.; 225:145-150; 2001), ferrimagnetic mineral, magnetite, chitosan, and affinity supports. The use of compositions including an immobilized-metal support material to capture or concentrate microorganisms from a sample is described in PCT Publication No. WO2008/134472, which is incorporated herein by reference in its entirety.

Exemplary particulate materials further include diatomaceous earth and surface treated diatomaceous earth. Specific examples of such concentration agents can be found in commonly assigned U.S. Patent Application Publication No. 2010/0209961, the disclosure of which is incorporated herein by reference. When dispersed or suspended in water systems, inorganic materials exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). In an embodiment, concentration agents can have zeta potentials that are at least somewhat more positive than that of untreated diatomaceous earth, and the concentration agents can be surprisingly significantly more effective than untreated diatomaceous earth in concentrating microorganisms such as bacteria, the surfaces of which generally tend to be negatively charged.

In some embodiments, the particulate material may comprise a binding partner coupled thereto and the binding partner may provide the specificity for binding a particular target analyte. In some embodiments, the particulate material may be incorporated into a matrix (e.g., beads entrapped in a fibrous matrix). FIG. 6B shows an exploded view of one configuration of an analyte-capture element 170' comprising a particulate material (e.g., hydroxyapatite particles). The analyte-capture element 170' is sandwiched between a porous support 172 and a porous shield 176. Both the porous support 172 and the porous shield 176 can be formed as described herein.

FIG. 5B shows a schematic side view of a portion of the fourth end 156 of a filtrate-receiving component 150', according to the present disclosure. In contrast to FIG. 5A, where the analyte-capture element 170 is disposed in the liner 158 disposed in the second chamber 160, sandwiched between a porous support 172 and a porous shield 176, the analyte-capture element 170 of this embodiment (e.g., a membrane filter) is releasably coupled to the second hollow body 152 (e.g., via an adhesive layer, not shown) at the second end 156. Other coupling means (e.g., sonic welding, heat-bonding) may be used, provided they don't substantially prevent contact between a liquid sample and the analyte-capture element 170 and/or substantially prevent the flow of a liquid sample through the analyte-capture element 170.

Figure 7A:
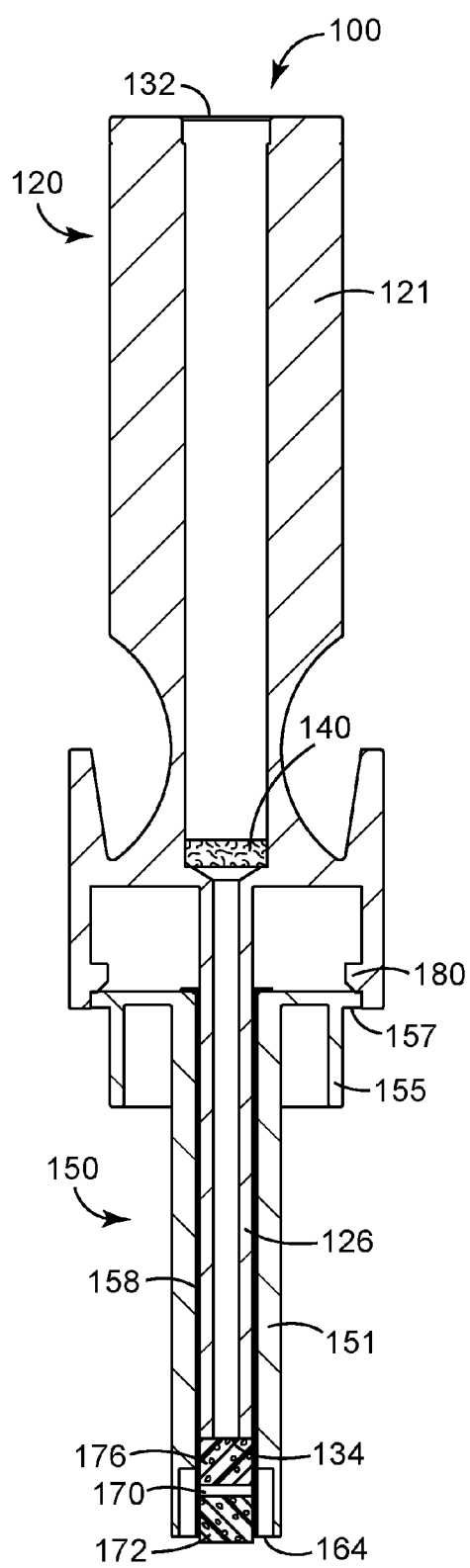
FIG. 7A is a cross-sectional side view of the apparatus of FIG. 2B.

FIG. 7A shows a cross-sectional side view of the first apparatus 100 of FIG. 2B in the first operational configuration. The second end 126 of the first hollow body 121 is shaped and proportioned to fit within and move longitudinally through at least a portion of the second chamber 160. In the first operational configuration, the second end 126 of the first hollow body 121 is inserted into the liner 158 which is disposed in the second chamber 160 of the second hollow body 151 to the extent that a substantially liquid-leak-resistant seal is formed by the outer surface of the second end 126 of the first hollow body 121 pressed against the liner 158 which, in turn, is pressed against the inner surface of the second hollow body 150. In the illustrated embodiment, it should be noted that, the second end 126 of the first hollow body 121 is inserted far enough into the second hollow body 151 to position the second opening 134 adjacent the porous shield 176. When the first apparatus 100 is placed in a first operational configuration, the second end 126 should be inserted far enough into the second hollow body 151 to form a seal, but it is not necessary that the second opening 134 is positioned immediately proximate the porous shield 176.

In the first operational position, the first apparatus 100 is ready to receive and process a sample. Thus, in the first operational position, a liquid flow path extending from the first opening 132 through the first chamber 130, the filter element 140, the second opening 134, the second chamber not shown, the fourth opening 164, and to or through the analyte-capture element 170, is formed. Either before or after placing the sample-receiving component 120 and the filtrate-receiving component into the first operational position, the filtrate-receiving component 150 can be coupled (e.g., via the collar 155) to a waste receptacle 300, as shown in FIG. 2. A liquid sample may then be transferred into the first chamber 130 through the first opening 132 and the sample can be drawn through the liquid flow path by applying negative pressure to the waste receptacle 300, if present, or by gravity flow.

The apparatus may be supported by a waste receptacle 300, as shown in FIG. 2A, when a liquid sample is transferred into the first chamber 130. The liquid sample (not shown) is transferred (e.g., by pouring or pipetting) into the first chamber 130 and allowed to pass through the filter element 140, into the second chamber 160, and into contact with and/or passage through analyte-capture element 170. In some embodiments, the liquid sample can pass through the device by gravity flow. In some embodiments, the liquid can be urged to pass through the first apparatus 100 by applying negative pressure to the fourth opening 164 (as shown in FIG. 2). Large volumes of liquid sample can be passed through the first apparatus 100 by passing two or more aliquots of the larger volume through the first apparatus 100 sequentially. In some embodiments, the volume of the first chamber 130 is at least about one milliliter. In some embodiments, the volume of the first chamber 130 is at least about five milliliters. In some embodiments, the volume of the first chamber 130 is at least about ten milliliters. In some embodiments, the volume of the first chamber 130 is at least about twenty-five milliliters. In some embodiments, the volume of the first chamber 130 is at least about one hundred milliliters.

After the liquid sample has passed through the first apparatus 100, the analyte-capture element 170 is separated from the first apparatus 100. Initially, the first apparatus 100 is detached from the waste receptacle 300, if said waste receptacle is used to draw the liquid sample through the first apparatus 100. The fourth end 156 of the first apparatus 100 is positioned over the opening of a container (e.g., a test tube, not shown) or, optionally, a container is detachably attached to the first apparatus 100 such that the opening of the container faces the fourth opening 164 of the apparatus, as shown in FIG. 2B. Force is applied to the sample-receiving component 120, the filtrate receiving component 150, or both such that they are urged together. The force should be sufficient to deflect the positioning element 180 outward as described above, thus allowing the second end 126 of the sample-receiving component 120 to further penetrate the second chamber 160 of the filtrate-receiving component 150, thereby placing the first apparatus 100 in a second operational configuration.

Figure 7B:
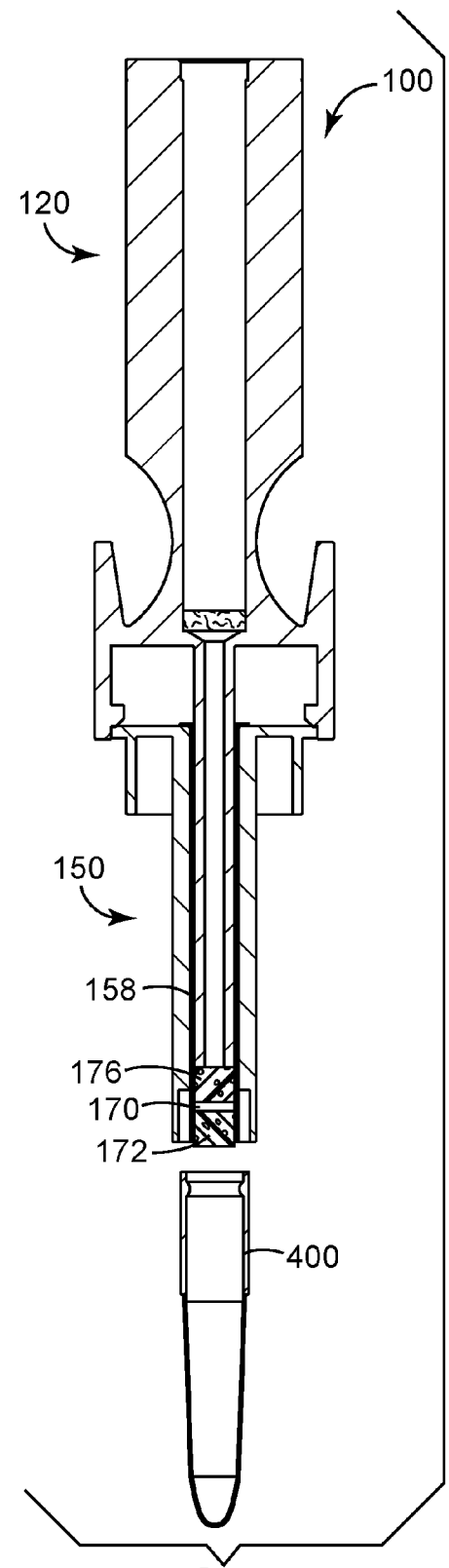
FIG. 7B is a cross-sectional side view of the assembled apparatus of FIG. 7A in a first operational configuration and a container.

FIG. 7B shows a partially-exploded cross-sectional view of the assembled first apparatus 100 and container 400 of FIG. 2B. It is noted that, when the first apparatus 100 is in this first operational configuration, liner 158 is disposed in the second chamber (not shown) of the filtrate-receiving component 150 and the second end 126 of the sample-receiving component 120 is slideably inserted into the liner 158. It is also noted that, in this configuration, the second end of the sample-receiving component 120 preferably should not penetrate the second chamber 160 to the extent that it displaces the porous shield 176, the analyte-capture element 170 or the porous support 172.

Figure 7C:
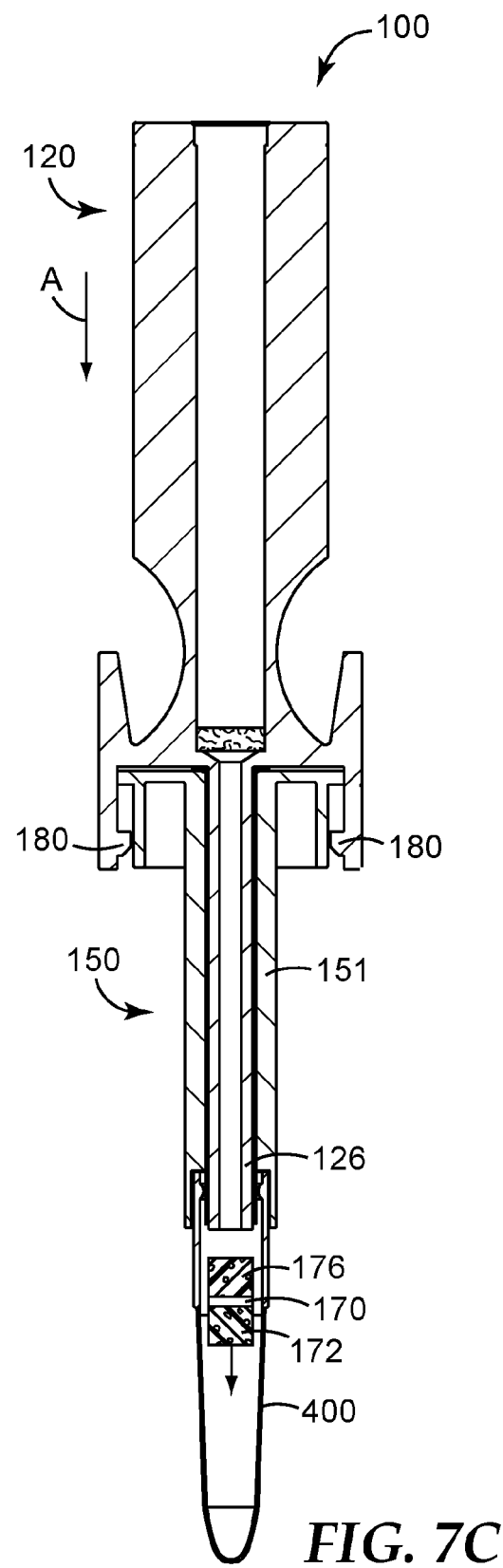
FIG. 7C is a cross-sectional side view of the assembled apparatus of FIG. 7B in a second operational configuration with the container operationally attached to the apparatus.

FIG. 7C shows a cross-sectional side view of the first apparatus 100 of FIG. 2C in a second operational configuration. In this configuration, the sample-receiving component 120 has been urged toward the filtrate-receiving component 150 until the positioning elements 180 reach a second position relative to the filtrate-receiving component 150. In this position, the second end 126 of the sample-receiving component 120 has moved far enough into the second hollow body 151 to displace the porous shield 176, the analyte-capture element 170 and the porous support 172, thereby causing the separation (e.g., ejection) of the porous shield 176, analyte-capture element 170, and the porous support 172 from the first apparatus 100. If the analyte-capture element 170 is not coupled to either the porous shield 176 or the porous support 172, they can spontaneously separate from one another. Advantageously, this can expose the analyte-capture element for subsequent treatment (e.g., contact with a cell lysis reagent). In this operational configuration, the analyte-capture element 170 conveniently is ejected into the container 400 for further processing as described herein.

Figure 8:
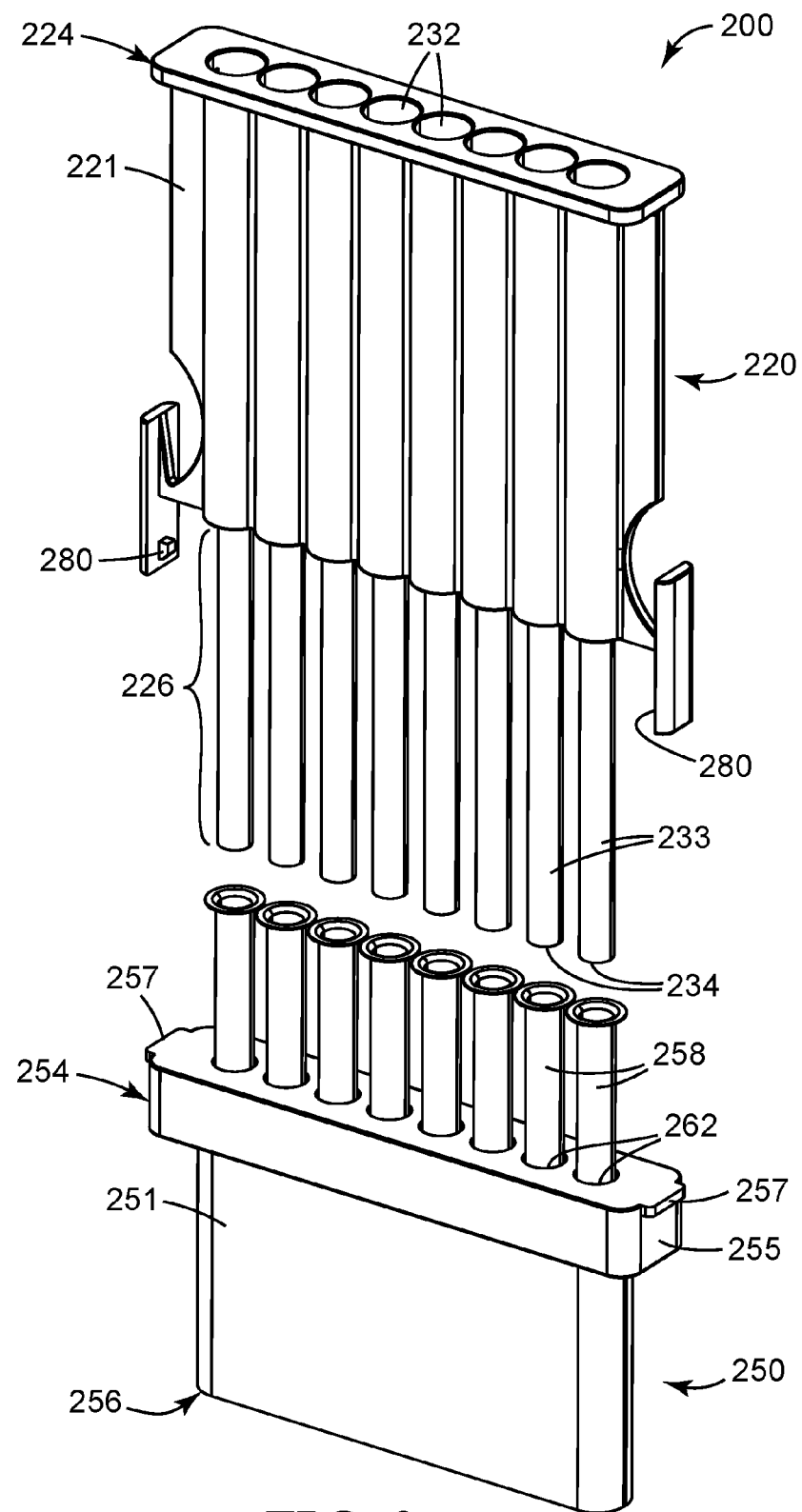
FIG. 8 is an exploded perspective view of one embodiment of an apparatus for processing a plurality of samples, according to the present disclosure.

In another aspect, the present disclosure provides an apparatus for processing a plurality of samples. FIG. 8 shows an exploded upper perspective view of one embodiment of a second apparatus 200 according to the present disclosure. It can be seen that the second apparatus 200 is similar to the first apparatus 100 of FIGS. 1-7 in structure and function except that second apparatus 200 is structurally configured to process a plurality of samples. In some embodiments, the samples may be processed in second apparatus 200 simultaneously.

The second apparatus 200 comprises a sample-receiving component 220 and a filtrate-receiving component 250. The sample-receiving component 220 comprises a first body 221 with a first end 224 and a second end 226 opposite the first end 224. The first end includes a plurality of first openings 232. The first openings 232 are configured to receive a sample. For example, the first openings 232 can be dimensioned to receive a pipette tip, through which a liquid sample can be transferred into the first hollow body 221. The second end comprises a plurality of outlets 233, each outlet having a second opening 234.

The sample-receiving component 220 further comprises optional positioning elements 280. The positioning element 280 can function temporarily to maintain the sample-receiving component 220 in a substantially fixed position relative to the filtrate receiving component 250, as shown and described for first apparatus 100 in FIGS. 2A-2C. The positioning element 280 may function cooperatively with structures found on the filtrate-receiving component 250, as shown and described for first apparatus 100 in FIGS. 2A-2C.

Also shown in FIG. 8 is an optional liner 258. If present, the liner 258 is dimensioned to be inserted through at least one of the plurality of the third openings 262 into the second hollow body 251. The liner 258 can be fabricated and used as described herein for the optional liner 158 that is used in first apparatus 100.

The filtrate-receiving component 250 comprises a second body 251 with a third end 254 and a fourth end 256 opposite the third end 254. The third end 254 includes a plurality of third openings 262. The third openings 262 are dimensioned to receive an outlet 233 of the sample-receiving component 220. Each of the plurality of outlets 233 is shaped and proportioned to fit within and move longitudinally through at least a portion of the second chamber 260. When the second apparatus 200 includes the optional liner 258, each of the plurality of outlets 233 of the sample-receiving component 220 is shaped and proportioned to be inserted into the liner 258. The filtrate-receiving component 250 further comprises an optional collar 255, which can facilitate coupling the second apparatus 200 to a source of negative pressure, similar to the coupling of first apparatus 100 to waste receptacle 300 as shown and described in FIG. 2A. Optionally, the collar 255 can further comprise tabs 257 to act in concert with the positioning element 280 to maintain the position of the sample-receiving component 220 relative to the filtrate-receiving component 250, as shown for first apparatus 100 in FIG. 2.

The first body 221 and/or the second body 251 can be fabricated by injection molding, for example, from polymeric material (e.g., polyethylene, polypropylene, polystyrene, polycarbonate). Alternatively, the first body 221 and/or the second body 251 can be fabricated using glass or metal.

Figure 9:
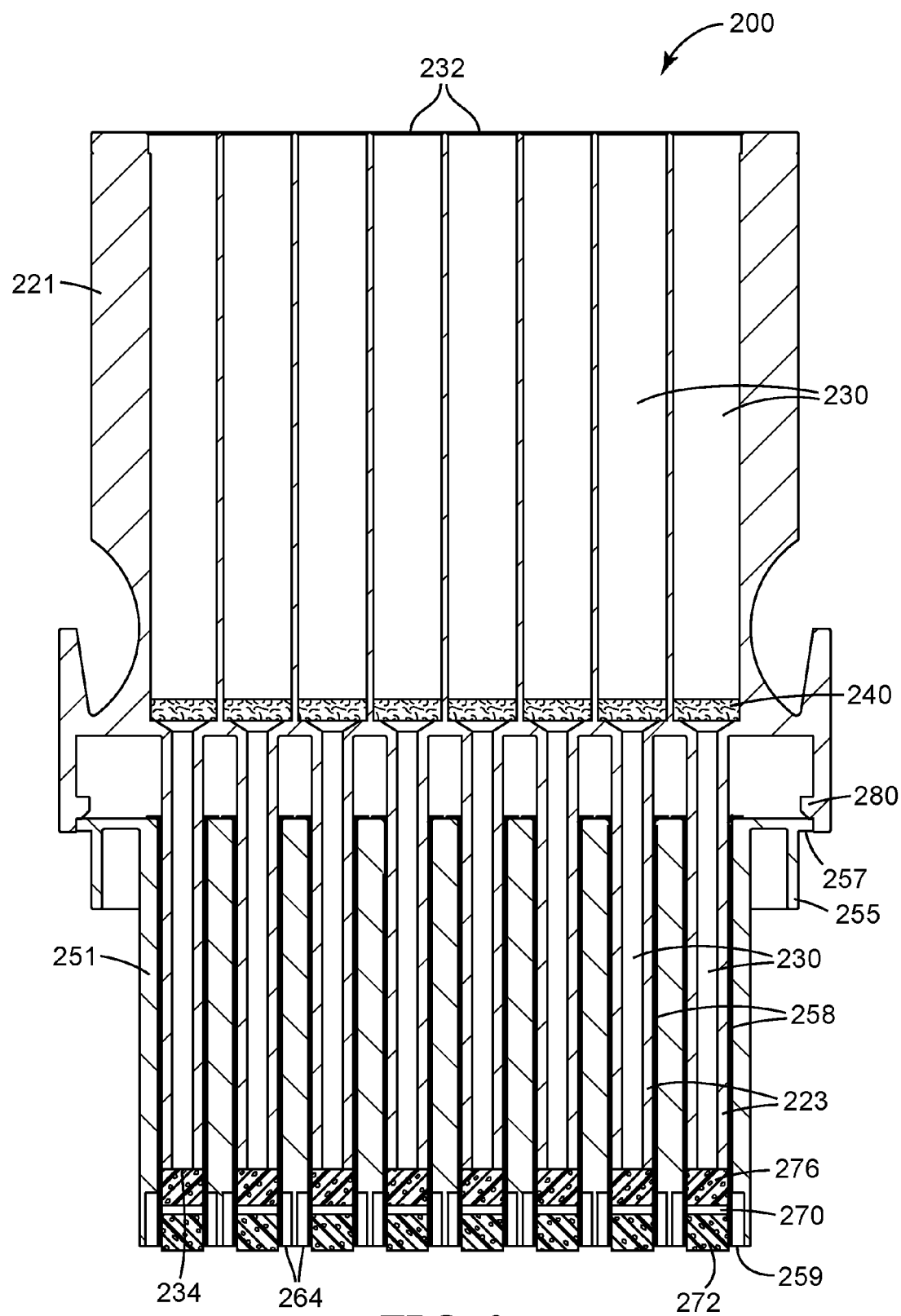
FIG. 9 is a cross-sectional side view of the apparatus of FIG. 8 in a first operational configuration.

FIG. 9 shows a cross-sectional side view of the second apparatus 200 of FIG. 8. The second apparatus 200 is in a first operational configuration (e.g., the positioning element 280 is contacting the tab 257) and, thus it is ready to receive a liquid sample into one or more of the plurality of first chambers 230. The illustrated embodiment shows that the assembled second apparatus 200 forms a plurality of liquid flow paths, each flow path extending from a first opening 232 through a first chamber 130, a filter element, a second chamber (not shown), and an analyte-capture element 170 that is disposed between a porous shield 176 and a porous support 172.

Figure 10:
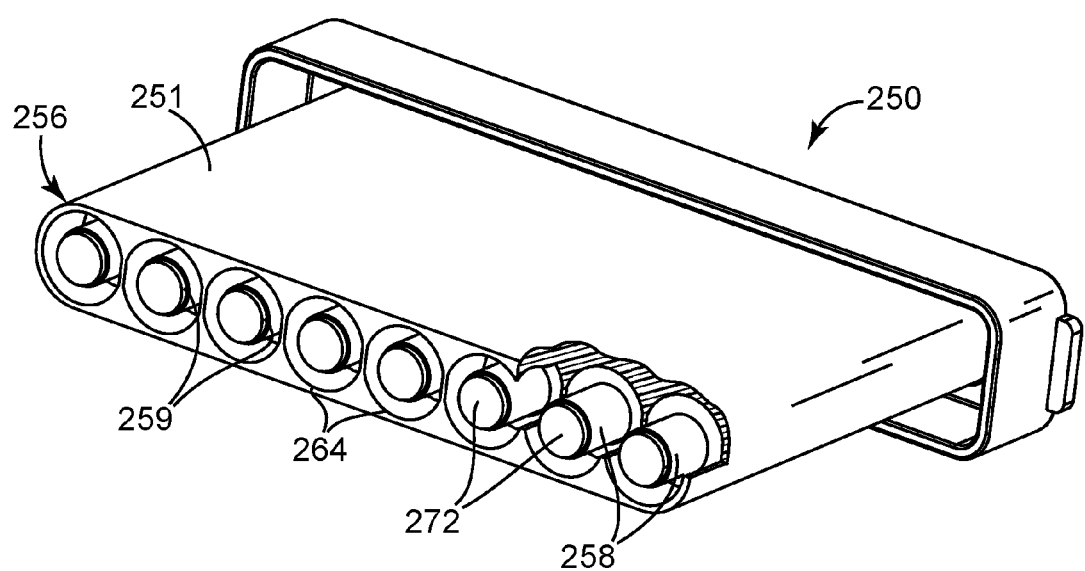
FIG. 10 is a bottom perspective view of the filtrate-receiving component of the apparatus of FIG. 9.

FIG. 10 shows a bottom perspective view, partially in section, of the second end 256 of the filtrate-receiving component 250 of the second apparatus 200 of FIG. 9. The fourth end 256 includes a plurality of fourth openings 264, which are shaped and proportioned to receive the open end of a container (e.g., a tube), as shown and described for first apparatus 100 in FIGS. 2B-2C. Also shown in FIG. 10 is a plurality of liners 258, each liner comprising a sixth opening 259. Disposed in each liner 258 proximate the sixth opening 259 is a porous support 272.

In one embodiment (not shown) of the first body, the first chambers are spaced apart in a configuration that permits the detachment of at least one liquid flow path (i.e., including the first chamber and the outlet connected there to) from at least one other of the plurality of liquid flow paths. Detaching the liquid flow path essentially results in formation of a first hollow body, as shown and described in FIG. 3. Optionally, each of the detachable liquid flow paths of this embodiment may further comprise a positioning element, as described herein.

Any embodiment of the first apparatus 100 or second apparatus 200 can be used in a method of processing a sample. Second apparatus 200 may be used to process one sample at a time or it may be used to process two or more samples simultaneously. The samples can be processed to detect the presence or absence of an analyte (e.g., a microorganism) in each sample. Advantageously, the apparatus of the present disclosure permits the removal of contaminating materials from a sample and the concentration of analytes from the sample in one simple step. The method comprises passing a liquid sample through the filter element 140. In some embodiments, the sample can be drawn through the filter element 140 using negative pressure (e.g., coupling the first apparatus 100 to a source of negative pressure 325, as described herein) to produce a filtered liquid.

The method further comprises contacting the filtered liquid with the analyte-capture element 170 to capture the analyte. In some embodiments, the filtration and capturing can be accomplished in a single step. In some embodiments, contacting the filtered liquid with the analyte-capture element can comprise passing the filtered liquid through a porous analyte-capture element (e.g., a membrane filter) to capture the analyte by adsorption or filtration, for example. In some embodiments, contacting the filtered liquid with the analyte-capture element can comprise placing the filtered liquid in fluid communication with a particulate analyte-capture element (e.g., hydroxyapatite, ion-exchange resins, antibody-coated particles) to capture the analyte by non-specific adsorption or by affinity binding, for example.

The method further comprises separating the analyte-capture element 170 from the first apparatus 100. Advantageously, the design of the first apparatus 100 and second apparatus 200 provides a simple means whereby the analyte-capture element 170 can be separated from the apparatus using one simple motion (e.g., urging the sample-receiving component and the filtrate-receiving component together causes a portion of the sample-receiving component to contact and eject the analyte-capture element from the filtrate-receiving component). Advantageously, the design of the first apparatus 100 and second apparatus 200 optionally permits a container 400 to be coupled to the apparatus before the analyte-capture element is separated. This permits the operator to eject the analyte-capture element from the first apparatus 100 directly into the detachably-attached container, thereby minimizing the handling and/or the possibility of contamination of the analyte-capture element. Additionally, the attached container 400 may further comprise a reagent to process an analyte captured by the analyte-capture element. The reagent may be chosen by the operator according to the particular analyte and detection method.

In some embodiments, the analyte may be a whole microorganism such as a bacterium, for example. In some embodiments, the analyte may be a living microorganism. In these embodiments, it may be desirable to detect the microorganism by culture techniques. Accordingly, the microorganisms may be detached or eluted from the analyte-capture element by rinsing and/or homogenizing the analyte-capture element in a suspending medium (water, buffer, buffered saline, liquid culture media). The liquid suspending medium could be used to inoculate culture media (e.g., the appropriate agar culture medium) to determine the presence, absence or quantity of target microorganisms that were in the original sample. In some embodiments, the analyte-capture medium could be transferred directly onto culture media for growth and analysis. Accordingly, when the analyte-capture element is separated from the apparatus by ejecting the analyte-capture element into a container, the container may include a suspending medium therein.

In some embodiments, the analyte may be a whole microorganism or a portion of a microorganism (e.g., a cell wall or a fragment thereof, a cell membrane or a fragment thereof, a protein, or a polysaccharide). In these embodiments, it may be desirable to detect the analyte using an immunodiagnostic method (e.g., ELISA, immunochromatography). Accordingly, when the analyte-capture element is separated from the apparatus by ejecting the analyte-capture element into a container, the container may include a suspending medium, a cell lysis reagent (e.g., an acid, a base, a detergent, an enzyme, a protease, lysozyme, lysostaphin), and/or an analyte-specific binding partner (e.g., an antibody, a receptor) therein.

In some embodiments, the analyte may be an enzyme or an enzyme substrate (e.g., ATP) associated with a particular microorganism or group of microorganisms. In these embodiments, it may be desirable to detect the analyte using an enzyme assay. Accordingly, when the analyte-capture element is separated from the apparatus by ejecting the analyte-capture element into a container, the container may include a suspending medium, a cell lysis reagent (e.g., an acid, a base, a detergent, an enzyme, a protease, lysozyme, lysostaphin), an enzyme (e.g., luciferase, adenylate kinase) and/or an enzyme substrate (e.g., a luciferin, a chromogenic enzyme substrate, or a fluorogenic enzyme substrate) therein.

In some embodiments, the analyte may be a microorganism-associated polynucleotide (e.g., DNA or RNA). In these embodiments, it may be desirable to detect the analyte using nucleic acid detection methods known in the art (e.g., PCR, rtPCR, LCR, NASBA, blot analysis). Accordingly, when the analyte-capture element is separated from the apparatus by ejecting the analyte-capture element into a container, the container may include a suspending medium, a cell lysis reagent (e.g., an acid, a base, a detergent, an enzyme, a protease, lysozyme, lysostaphin), an analyte-specific probe, an analyte-specific primer and/or an enzyme and a reagent for amplifying or labeling a polynucleotide therein.

In some embodiments, the method further can comprise an enrichment step. The enrichment step can comprise providing a culture medium to facilitate the growth of a target microorganism and a latent effervescent body comprising a selective agent, as described in PCT Publication No. WO2012/092123, which is incorporated herein by reference in its entirety.

EMBODIMENTS

Embodiment 1 is an apparatus for processing a sample, comprising:
a sample-receiving component;
a filtrate-receiving component; and
an analyte-capture element;
wherein the sample-receiving component comprises:
a first hollow body with first end, a second end, and a first chamber extending from the first end to the second end; and
a filter element disposed in the first chamber between the first and second ends;
wherein the first end includes a first opening configured to receive a sample;
wherein the second end includes a second opening;
wherein the filtrate-receiving component comprises a second hollow body with a third end, a fourth end, and a second chamber extending from the third end to the fourth end; and ;
wherein the third end includes a third opening configured to receive the second end of the sample-receiving member;
wherein the fourth end includes a fourth opening;
wherein, the analyte-capture element is removably coupled to the filtrate-receiving component;
wherein, when the sample-receiving component is coupled to the filtrate-receiving component, the apparatus forms a flow path that facilitates fluid passage through the first chamber, the filter element, and the second chamber, the flow path facilitating contact between a fluid sample and the analyte-capture element;
wherein the second end is shaped and proportioned to fit within and move longitudinally through at least a portion of the second chamber.

Embodiment 2 is the apparatus of embodiment 1, wherein the analyte-capture element further is disposed in the second chamber.

Embodiment 3 is the apparatus of any one of the preceding embodiments, further comprising a removable inner sleeve with a fifth end having a fifth opening and a sixth end having a sixth opening, wherein the sleeve is disposed in the second chamber.

Embodiment 4 is the apparatus of any one of the preceding embodiments, further comprising a porous support or a porous shield.

Embodiment 5 is the apparatus of embodiment 4, wherein at least a portion of the porous support or at least a portion of the porous shield is disposed in the second hollow body between the analyte-capture element and the fourth opening.

Embodiment 6 is the apparatus of embodiments 4 or embodiment 5, wherein the analyte-capture element is coupled to the porous support or porous shield.

Embodiment 7 is the apparatus of any one of the preceding embodiments, wherein the filter element further comprises a plurality of layers.

Embodiment 8 is the apparatus of any one of embodiments 1 through 7, wherein the second end is adapted to be inserted into the second chamber and moved through the second hollow body to a point at which it contacts the analyte-capture element, porous support, or porous shield.

Embodiment 9 is an apparatus for processing a plurality of samples, comprising:
a sample-receiving component;
a filtrate-receiving component; and
a plurality of analyte-capture elements;
wherein the sample-receiving component comprises:
a first body with first end, a second end, and a plurality of spaced-apart first chambers, each first chamber extending from the first end to the second end;
wherein the first end comprises a plurality of first openings, at least one first opening configured to receive a sample;

wherein the second end comprises a plurality of outlets, each outlet having a second opening;

wherein the first body forms a plurality of fluid pathways, each pathway extending from a first opening to a second opening and through a first chamber there between; and a plurality of filter elements, each filter element disposed between the first and second openings in one of the plurality of first chambers;

wherein the filtrate-receiving component comprises:

a second body with a third end, a fourth end, and a plurality of spaced-apart second chambers, each second chamber extending from the third end to the fourth end and each second chamber comprising:

a third opening at the third end, the third opening configured to receive one of the plurality of outlets;

a fourth opening at the fourth end;

wherein each of the plurality of analyte-capture elements is coupled to the filtrate-receiving component;

wherein, when the sample-receiving component is coupled to the filtrate-receiving component, the apparatus forms a plurality of flow paths, each flow path facilitating fluid passage through one of the plurality of first chambers, one of the plurality of filter elements, and one of the plurality of second chambers, and facilitating fluid contact with at least one of the plurality of analyte-capture elements;

wherein each of the plurality of outlets is shaped and proportioned to fit within and move longitudinally through at least a portion of the second chamber.

Embodiment 10 is the apparatus of embodiment 9, wherein at least one of the plurality of analyte-capture elements further is disposed in at least one of the plurality of second chambers.

Embodiment 11 is the apparatus of embodiment 9 or embodiment 10, further comprising at least one removable inner sleeve with a fifth end having a fifth opening and a sixth end having a sixth opening, wherein the sleeve is disposed in at least one of the plurality of second chambers.

Embodiment 12 is the apparatus of any one of embodiments 9 through 11, further comprising at least one porous support or at least one porous shield.

Embodiment 13 is the apparatus of embodiment 12, wherein at least a portion of the at least one porous support or at least one porous shield is disposed in at least one second chamber between the analyte-capture element and the fourth end.

Embodiment 14 is the apparatus of any one of embodiments 12 through 13, wherein the analyte-capture element is coupled to the porous support.

Embodiment 15 is the apparatus of any one of embodiments 9 through 14, wherein the at least one filter element further comprises a plurality of layers.

Embodiment 16 is the apparatus of any one of embodiments 9 through 15, wherein each of the plurality of outlets is adapted to be inserted into one of the plurality of second chambers and moved through the second chamber to a point at which it contacts the analyte-capture element, porous support, or porous shield.

Embodiment 17 is the apparatus of any one of embodiments 1 through 16, wherein the filtrate-receiving component is configured to couple to a source of negative pressure.

Embodiment 18 is the apparatus of any one of embodiments 1 through 17, wherein at least one of the sample receiving component or filtrate-receiving component further comprises a positioning element that, when the sample-receiving component is coupled to the filtrate-receiving component, controllably retains a position of the sample-receiving component relative to the filtrate-receiving component.

Embodiment 19 is a method of detecting the presence or absence of an analyte in a sample, comprising:

providing a liquid sample and the apparatus of any one of embodiments 1 through 8;

passing the liquid sample through the filter element;

contacting the filtered liquid with the analyte-capture element;

separating the analyte-capture element from the apparatus; and detecting the presence or absence of the analyte.

Embodiment 20 is the method of embodiment 19, further comprising attaching the apparatus to a source of negative pressure, wherein passing the liquid sample through the filter element further comprises using a negative pressure to draw the sample through the filter element to produce a filtered sample.

Embodiment 21 is the method of embodiment 20, wherein using negative pressure to draw the sample through the filter element further comprises using the negative pressure to contact the filtered sample with the analyte-capture element.

Embodiment 22 is the method of any one of embodiments 19 through 21, wherein separating the analyte-capture element from the apparatus further comprises using the second end to separate the analyte-capture element.

Embodiment 23 is the method of embodiment 22, wherein using the second end further comprises urging the second end through the second chamber to separate the analyte-capture element.

Embodiment 24 is the method of any one of embodiments 19 through 23 further comprising, after separating the analyte-capture element, treating the analyte-capture element with a cell lysis agent.

Embodiment 25 is a method of detecting the presence or absence of an analyte in a plurality of sample, comprising:

providing a plurality of liquid samples and the apparatus of any one of embodiments 9 through 18;

passing at least two liquid sample through at least two of the plurality of filter elements to generate at least two filtered liquids;

contacting the at least two filtered liquids with at least two analyte-capture elements;

separating the at least two analyte-capture elements from the apparatus; and detecting the presence or absence of the analyte.

Embodiment 26 is the method of embodiment 25, further comprising attaching the apparatus to a source of negative pressure, wherein passing the plurality liquid samples through the at least two filter element further comprises using a negative pressure to draw the liquid samples through the at least two filter elements to produce at least two filtered samples.

Embodiment 27 is the method of embodiment 26, wherein using negative pressure to draw the plurality of samples through the at least two filter elements further comprises using the negative pressure to contact the filtered samples with the at least two analyte-capture elements.

Embodiment 28 is the method of any one of embodiments 25 through 27, wherein separating the at least two analyte-capture elements from the apparatus further comprises using at least two outlets to separate the at least two analyte-capture elements from the apparatus.

Embodiment 29 is the method of embodiment 28, wherein using the at least two outlets further comprises urging the at least two outlets through the at least two second chambers to separate the at least two analyte-capture elements from the apparatus.

Embodiment 30 is the method of any one of embodiments 25 through 29 further comprising, after separating the at least two analyte-capture elements, treating the at least two analyte capture element with a cell lysis agent.

Various modifications may be made without departing from the spirit and scope of the invention. These and other embodiments are within the scope of the following claims.

The invention claimed is:

1. An apparatus for processing a sample, comprising:
   a sample-receiving component;
   an filtrate-receiving component; and
   an analyte-capture element;
   wherein the sample-receiving component comprises:
   a first hollow body with first end, a second end, and a first chamber extending from the first end to the second end;
   a filter element disposed in the first chamber between the first and second ends; and
   optionally, a porous shield or a porous support;
   wherein the first end includes a first opening configured to receive a sample;
   wherein the second end includes a second opening;
   wherein the filtrate-receiving component comprises a second hollow body with a third end, a fourth end, and a second chamber extending from the third end to the fourth end;
   wherein the second end is adapted to be inserted into the second chamber and moved through the second hollow body to a point at which it contacts the analyte-capture element, porous support, or porous shield;
   wherein the third end includes a third opening configured to receive the second end of the sample-receiving member;
   wherein the fourth end includes a fourth opening;
   wherein, the analyte-capture element is removably coupled to the filtrate-receiving component;
   wherein, when the sample-receiving component is coupled to the filtrate-receiving component, the apparatus forms a flow path that facilitates fluid passage through the first chamber, the filter element, and the second chamber, the flow path facilitating contact between a fluid sample and the analyte-capture element;
   wherein the second end is shaped and proportioned to fit within and move longitudinally through at least a portion of the second chamber.

2. The apparatus of claim 1, wherein the analyte-capture element further is disposed in the second chamber.

3. The apparatus of claim 1, further comprising a removable inner sleeve with a fifth end having a fifth opening and a sixth end having a sixth opening, wherein the sleeve is disposed in the second chamber.

4. The apparatus of claim 1, wherein at least a portion of the porous support or at least a portion of the porous shield is disposed in the second hollow body between the analyte-capture element and the fourth opening.

5. The apparatus of claim 1, wherein the analyte-capture element is coupled to the porous support or porous shield.

6. The apparatus of claim 1, wherein the filter element further comprises a plurality of layers.

7. The apparatus of claim 1, wherein the fourth end is configured to couple to a source of negative pressure.

8. The apparatus of claim 1, wherein at least one of the sample receiving component or filtrate-receiving component further comprises a positioning element that, when the sample-receiving component is coupled to the filtrate-receiving component, controllably retains a position of the sample-receiving component relative to the filtrate-receiving component.

9. A method of detecting the presence or absence of an analyte in a sample, comprising:
   providing a liquid sample and the apparatus of claim 1;
   passing the liquid sample through the filter element;
   contacting the filtered liquid with the analyte-capture element;
   separating the analyte-capture element from the apparatus; and
   detecting the presence or absence of the analyte.

10. The method of claim 9, further comprising attaching the apparatus to a source of negative pressure, wherein passing the liquid sample through the filter element further comprises using a negative pressure to draw the sample through the filter element to produce a filtered sample.

11. The method of claim 10, wherein using negative pressure to draw the sample through the filter element further comprises using the negative pressure to contact the filtered sample with the analyte-capture element.

12. The method of claim 9, wherein separating the analyte-capture element from the apparatus further comprises using the second end to separate the analyte-capture element from the apparatus.

13. The method of claim 12, wherein using the second end further comprises urging the second end through the second chamber to separate the analyte-capture element from the apparatus.

14. The method of claim 9 further comprising, after separating the analyte-capture element, treating the analyte capture element with a cell lysis agent.

* * * * *